US008545518B2

(12) United States Patent
Grieshaber et al.

(10) Patent No.: US 8,545,518 B2
(45) **Date of Patent: *Oct. 1, 2013**

(54) HYBRID EPILATOR DEVICE

(75) Inventors: Frieder Grieshaber, Neu-Anspach (DE); Bernd Pfeiffer, Schwalbach (DE); Bernhard Kraus, Braunfels (DE)

(73) Assignee: Braun GmbH, Kronberg (DE)

( * ) Notice: Subject to any disclaimer, the term of this patent is extended or adjusted under 35 U.S.C. 154(b) by 160 days.

This patent is subject to a terminal disclaimer.

(21) Appl. No.: 12/763,261

(22) Filed: Apr. 20, 2010

(65) Prior Publication Data

US 2010/0274261 A1 Oct. 28, 2010

(30) Foreign Application Priority Data

Apr. 27, 2009 (EP) .................................... 09005828

(51) Int. Cl.
*A61B 17/50* (2006.01)

(52) U.S. Cl.
USPC .......................................................... 606/133

(58) Field of Classification Search
USPC ........ 606/36, 43, 133, 144; 30/34.2; 451/71, 451/82, 83, 84, 85, 86, 102, 103, 104
See application file for complete search history.

(56) References Cited

U.S. PATENT DOCUMENTS

| | | | |
|---|---|---|---|
| 5,980,452 A | 11/1999 | Garenfeld et al. | |
| 2005/0216035 A1* | 9/2005 | Kraus et al. | 606/133 |
| 2005/2886873 | 12/2005 | Dorber et al. | |
| 2008/0196258 A1 | 8/2008 | Kraus | |
| 2008/0301947 A1 | 12/2008 | Dorber et al. | |
| 2010/0234858 A1* | 9/2010 | Sanchez-Martinez et al. | 606/133 |
| 2011/0094106 A1* | 4/2011 | Kling et al. | 30/34.1 |

FOREIGN PATENT DOCUMENTS

| | | |
|---|---|---|
| EP | 1797788 | 6/2007 |
| JP | 56-100088 A | 8/1981 |
| JP | 4126103 | 4/1992 |
| JP | 10-151020 A | 6/1998 |
| JP | 2000-060629 A | 2/2000 |
| JP | 2004-141327 A | 5/2004 |
| JP | 2006-149489 A | 6/2006 |
| WO | WO-2006/037392 A1 | 4/2006 |
| WO | WO-2009052880 | 4/2009 |

OTHER PUBLICATIONS

European Search Report dated Jul. 15, 2009 containing 4 pages.

* cited by examiner

*Primary Examiner* — Thomas McEvoy
(74) *Attorney, Agent, or Firm* — Jeffrey V Bamber; Jerry J Yetter

(57) ABSTRACT

The present invention is a hybrid epilator device comprising an epilation unit for gripping and plucking hairs from a skin surface and at least one razor blade edge to shave off hairs growing on the skin surface. The blade edge defines a use direction along which it is effectuated that hairs are shaved off when the razor blade is drawn over the skin surface during operation. The razor blade is arranged behind the epilation unit with respect to the use direction. The epilation unit and the razor blade are mounted for simultaneous contact with the skin surface, where during operation the epilation unit grips and plucks out hairs from the skin surface and subsequently the razor blade shaves off remaining hairs growing on the same skin surface in a single stroke.

12 Claims, 3 Drawing Sheets

HYBRID EPILATOR DEVICE

FIELD OF THE INVENTION

The present invention is concerned with a hybrid epilator device and in particular with a hybrid epilator device that comprises a razor blade.

BACKGROUND OF THE INVENTION

A hybrid epilator device comprising a razor blade was first described in German patent application No. 102007050661.0-23

SUMMARY OF THE INVENTION

It is now desirable to provide an improved hybrid epilator device that allows for more convenient usage.

Such a hybrid epilator device is given in accordance with claim 1. Further embodiments are given in accordance with the dependent claims.

The hybrid epilator device as proposed comprises an epilation unit for gripping and plucking out hairs from a skin surface and a razor blade that has a sharp edge for shaving off hairs from the skin surface. The sharp edge of the razor blade only allows for effective shaving operation when the hybrid epilator device is drawn over the skin surface along a certain use direction. The razor blade and the epilation unit are mounted for simultaneous contact of the skin surface. The razor blade is arranged behind the epilation unit with respect to the use direction so that during operation first the epilation unit grips and plucks out hairs from a certain skin surface and then the razor blade shaves off remaining hairs that are still present on the already epilated skin surface in the same single stroke with which the hybrid epilator device is drawn over the skin surface. The hybrid epilator device further comprises a control unit for controlling the epilation efficiency of the epilation unit. The epilation efficiency of the epilation unit is the ratio of the number of hairs plucked out from a certain skin surface area in a single stroke and the number of hairs that were present on this skin surface area prior to epilation. E.g. if ten hairs grow on a certain skin area and (in average) the epilation unit plucks out nine hairs from this skin surface area in a single stroke, then the epilation efficiency is 0.9 or 90%. As it can be assumed without prejudice that the subsequent shaving operation performed by the razor blade removes all remaining hairs, the total hair removal efficiency of the hybrid hair removal device is 100% per single stroke.

In an embodiment of the hybrid epilator device, the hybrid epilator device comprises an input unit for setting an epilation efficiency value that should be achieved by the hybrid epilator device. The control unit then controls the epilation efficiency of the epilation unit so that the set epilation efficiency is achieved. This allows for varying the epilation efficiency by the user and hence the user can vary the ratio of hairs that are plucked out from the skin surface and the number of hairs that are shaved off. Thereby, the amount of pain induced by the hair removal procedure can be varied and adapted according to the user's preference.

In another embodiment of the hybrid epilator device, the hybrid epilator device comprises a memory unit in which a preset epilation efficiency value is stored that is used by the control unit to control the epilation unit such that this preset epilation efficiency value is achieved in operation. In particular, this preset epilation efficiency value is smaller than the epilation efficiency that is achieved by the epilation unit without any control; e.g. the epilation unit may have a typical epilation efficiency of 90% but a general user preferred epilation efficiency for a hybrid epilator device may be 50%, so that the preset epilation efficiency value is 0.5 or 50%.

In a further embodiment of the hybrid epilator device, the control unit controls the plucking speed of the epilation unit to control the epilation efficiency. In particular, if the epilation unit comprises an epilation cylinder, then the control unit controls the rotation speed of the epilation cylinder as the rotation speed of the epilation cylinder relates to the plucking speed.

In an even further embodiment of the hybrid epilator device, the epilation unit comprises at least a pair of tweezers that is arranged to be actuated between an open position in which a gap is present between the clamping surfaces of the clamping elements forming the pair of tweezers and a closed position in which the clamping surface are in tight contact. The control unit controls the epilation efficiency by controlling a dynamic parameter of the actuation. In an refinement of this embodiment, the dynamic parameter is the width of the gap present in the open position (the smaller the gap the less hairs can feed in between the clamping elements and the lower the epilation efficiency becomes). In another refinement of this embodiment, the dynamic parameter is the angular position at which the closed position is assumed with respect to a housing of the hybrid epilator device. A variation and the closing position will also lead to a variation of the epilation efficiency.

In an embodiment of the hybrid epilator device, the hybrid epilator device comprises a velocity sensor to measure the speed with which the hybrid epilator device is drawn over the skin surface. In a refinement of this embodiment, the control unit is arranged to control the epilation efficiency in dependence on a speed signal provided by the velocity sensor. This allows e.g. for keeping the epilation efficiency constant even if the user varies the drawing speed or to achieve that the set (preset) epilation efficiency value is always reached even if different users apply different drawing speeds.

In another embodiment of the hybrid epilator device, the razor blade (or a cartridge in which the razor blade is mounted) is mounted so as to be floatable and/or pivotable with respect to the housing of the hybrid epilator device.

BRIEF DESCRIPTION OF THE DRAWINGS

The invention will be further described and elucidated by a description of exemplary embodiments of a hybrid epilator device as proposed and with reference to figures. In the figures

DETAILED DESCRIPTION OF THE INVENTION

Figure 1:
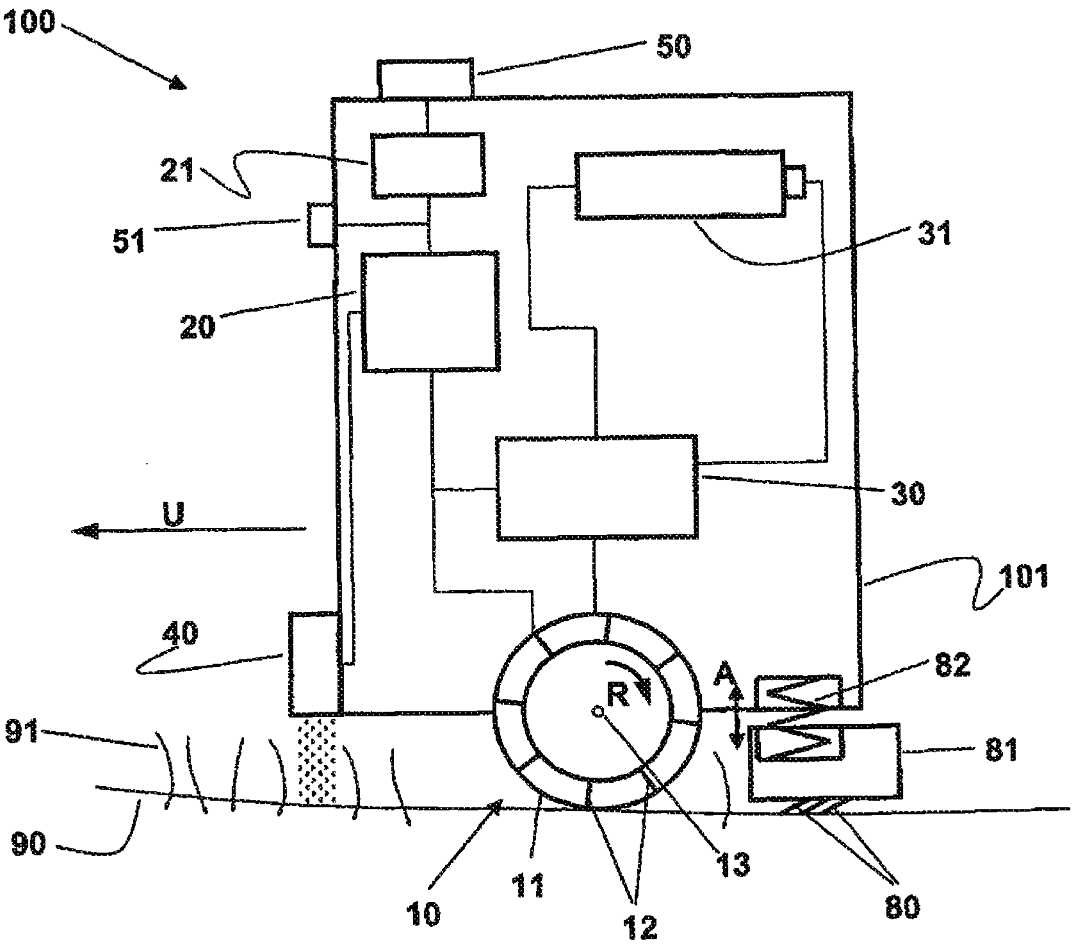
FIG. 1 shows a schematic depiction of an exemplary embodiment of a hybrid epilator device as proposed.

FIG. 1 shows a schematic depiction of an exemplary embodiment of a hybrid epilator device 100 as proposed. The hybrid epilator device 100 comprises a housing 101 at which an epilation unit 10 is mounted as is known in the art; e.g. international patent application WO 2006/037392 A1, the content of which is incorporated herein by reference, describes such a typical epilation unit and its mounting arrangement. The epilation unit 10 is arranged for gripping and plucking out hairs 91 growing on a skin surface 90 during regular operation of the hybrid epilator device 100. A motor

30 is coupled to the epilation unit 10 for driving the epilation unit 10 during operation. An energy source 31 (e.g. a primary or secondary battery) is coupled to the motor 30 to provide the necessary energy. Alternatively or additionally the hybrid epilator device 100 may be connectable to mains voltage via a cord. Here, the epilation unit 10 comprises an epilation cylinder 11 that has axially and circumferentially spaced pairs of tweezers 12 arranged at its outer surface. The epilation cylinder 11 is arranged for driven rotation around its central axis 13 as indicated by arrow R. An actuation system, as is e.g. also described in WO 2006/037392 A1, actuates in operation the pairs of tweezers between an open position, in which a gap is present between the clamping elements forming a pair of tweezers 12 so that hairs 91 can feed in between the clamping elements and a closed position, in which the hairs 91 are gripped between the clamping elements and are subsequently plucked out from the skin surface 90 while the epilation cylinder 11 continues to rotate. The actuation system is arranged such that the clamping elements assume a closed position at a circumferential position when the pair of tweezers is proximate the skin surface 90 during operation. The exact position may depend on the precise realization of the hybrid epilator device 100 to guarantee a high plucking efficiency. The hybrid epilator device 100 further comprises at least a razor blade 80, where in the embodiment shown in FIG. 1 three razor blades 80 are mounted in a cartridge 81 e.g. as is generally known in the art of safety razors. The cartridge 81 is floatingly mounted at the housing 101 by means of a spring element 82 that allows a vertical displacement of the cartridge 81 under an applied force with which the hybrid epilator device is pressed against the skin surface 90 as indicated by the double arrow A. Additionally or alternatively, the cartridge 81 may also be pivotably mounted with respect to the housing 101. Such a floatingly and/or pivotably mounted razor blade 80 always assumes an optimal close contact with the skin surface 90 even if the hybrid epilator device is pressed against the skin surface with a different angle as advised or if the skin surface topology is uneven as, e.g., around the knee or in the armpit etc. Hence, it is obvious that a floatingly and/or pivotable mounted razor blade 80 (or cartridge 81 comprising one or several razor blades 80) is beneficial as such for a hybrid epilator device 100 also without all the other features of the hybrid epilator device as described in the present application. The razor blade 80 comprises a sharp edge that is intended to shave off hairs 91 from the skin surface 90 during operation. Due to the sharp edge of the razor blade 80, which is only effective when it is drawn over the skin surface 90 at a certain angle with respect to the skin surface, a use direction U of the hybrid epilator device 101 is defined that allows shaving off hairs 91 from the skin surface 90. The razor blade 80 is arranged behind the epilation unit 10 with respect to the use direction U. The use direction U also coincides with the preferred use direction of the epilation unit 10. The epilation unit 10 and the razor blade 80 are mounted for simultaneous contact of the skin surface 90 such that during operation, when the hybrid epilator device 100 is drawn over the skin surface 90 in the use direction U, the epilation unit 10 first grips and plucks out hairs 91 from the skin surface 90 and the razor blade 80 shaves off remaining hairs that were not plucked out from the skin surface 90. Depending on its precise realization, an epilation unit 10 as known in the art may have an epilation efficiency of up to about 90%, which means that under optimal conditions (e.g. hairs have a certain minimal length, drawing velocity is adapted to the epilation unit 10, angle of the hybrid epilator device 100 with respect to the skin surface 90 is as advised) nine out of ten hairs 91 are gripped and plucked out from the skin surface 90 in a single stroke of the hybrid epilator device 100 (the epilation efficiency is hence the ratio of the number of plucked out hairs in a single stroke over a certain skin surface area and the number of hairs present on the skin surface area before epilation). It can now be assumed without prejudice that the razor blade 80 shaves off all remaining hairs 91 that were not plucked out by the epilation unit 10 in the same single stroke. Hence, the hybrid epilator device 100 has a hair removal efficiency of (almost) 100%. In addition to this (almost) perfect hair removal efficiency in a single stroke, the hybrid epilator device 100, specifically when used in a wet environment, e.g. in combination with a shaving lotion, generates a gentle and smooth skin feeling that is not reached with a pure epilation device, as the razor blade 80 also abrades top skin parts. Such a hybrid epilator device 100 is hence specifically fast in achieving complete hair removal on a certain skin surface area (e.g. a leg) and it also reduces the pain involved with plucking out hairs as hairs not plucked out in the first stroke are shaved off.

The hybrid epilator device 100 as proposed also comprises a control unit 20 that controls the epilation efficiency of the epilation unit 10. The hybrid epilator device 100 may comprise a memory unit 21 in which a preset epilation efficiency value is stored. This preset epilation efficiency value may be lower than the epilation efficiency that can be usually achieved with the present epilation unit 10. E.g. preset epilation efficiency value may be stored that is adapted to a general user favored ratio between plucked hairs and shaved hairs (such a generally favored epilation efficiency for a hybrid epilator device may be found by extensive consumer tests and may differ between territories). In order to reduce the achievable plucking efficiency of the epilation unit 10, the control unit 20 may influence the rotation speed of the epilation cylinder 11 by controlling the motor 30. A lower rotation speed (and hence a lower hair plucking speed) reduces the epilation efficiency. Further, the skin coverage of subsequent plucking events performed by the pairs of tweezers 12 may become incomplete. European patent application No. 08012880.4, the respective content of which application is incorporated herein by reference, describes the interaction of rotation speed and drawing speed and the effect these two parameters have on the epilation efficiency in more detail. Alternatively or additionally, the control unit 20 may influence the actuation unit such that the gaps between the clamping elements of the pairs of tweezers 12 are smaller than usual, which also leads to less hairs 91 feeding in between the clamping elements in the open position as usual. Such a control of the actuation system may be accomplished by arranging respective parts of the actuation system displaceable and controlling the displacement (e.g. performed by a stepping motor) by the control unit 20. Alternatively or additionally, the control unit 20 may influence the actuation system such that the position at which the closed position is assumed is varied, e.g. the closed position may be assumed at a larger angle with respect to the skin surface 90 such that hairs 91 that may have fed in between the clamping elements have slipped out of the gap between the clamping elements already when the closed position is assumed, which also leads to less plucked out hairs 91. The preset epilation efficiency value may hence be 50% instead of about 90%.

In order to allow a user to set an epilation efficiency value (in other words: to allow the user to set the ratio between plucked hairs causing pain and shaved off hairs that are removed without pain), the hybrid epilator device 100 may comprise an input unit 50 via which the user can set an individually favored epilation efficiency. E.g., some users may prefer an epilation efficiency value of 70% as they consider the higher plucking ratio as preferable with respect to the overall hair removal result over time while other user may prefer a lower epilation efficiency value such as 30% to reduce the epilation pain as much as possible. The user set epilation efficiency value is then communicated to the control unit 20 that accordingly controls the motor 30 or the actuation system as described above to achieve the user set epilation efficiency. The control unit 20 may comprise a reference table from which control parameters are received that relate to a certain epilation efficiency value (e.g. rotation speed of the epilation cylinder, gap between the clamping elements of the pairs of tweezers in the open position etc.). The hybrid epilator device 100 may also comprise a display unit 51 to indicate the currently applied epilation efficiency. E.g. the hybrid epilator device 100 may comprise three light emitting diodes that are assigned to an epilation efficiency of 30%, 50%, and 70%, respectively, and that are accordingly switched on/off by the control unit 20 in dependence of the applied epilation efficiency.

The hybrid epilator device 100 may further comprise a velocity sensor 40 for measuring the velocity with which the hybrid epilator device 100 is drawn over the skin surface 90. The velocity sensor 40 may be realized as an optical sensor such as a known from a computer mouse or as a mechanical sensor, e.g. a wheel that couples to the skin and rotates in accordance with the drawing speed. The velocity sensor 40 then communicates a respective velocity signal to the control unit 20. The control unit 20 then controls the epilation unit 10 such that the preset or individually set epilation efficiency value is achieved even if different users apply different drawing speeds. Alternatively or additionally, the control unit 20 may also be arranged to keep the epilation efficiency constant even if the drawing speed varies, e.g. by modifying the rotation speed of the epilation cylinder 11 by control of the motor 30 in dependence on the velocity signal.

Figure 2:
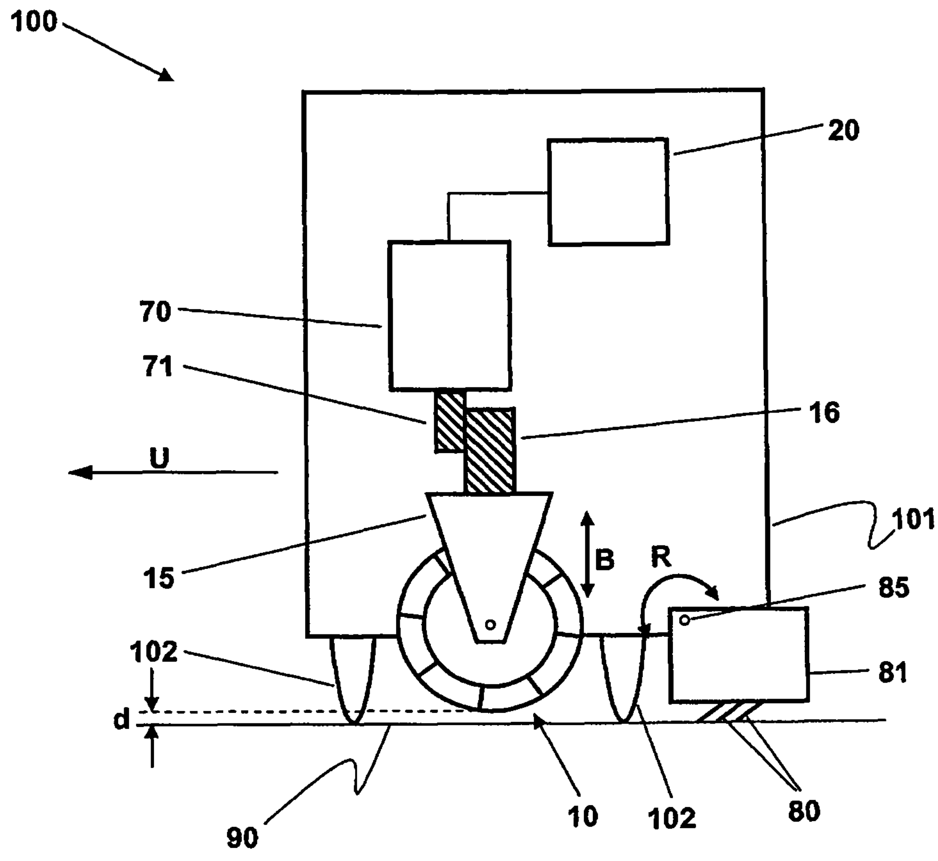
FIG. 2 shows a schematic depiction of a further exemplary embodiment of a hybrid epilator device as proposed.

FIG. 2 is a schematic depiction of a further exemplary embodiment of a hybrid epilator device as proposed. Optional features shown in FIG. 1 are not shown in FIG. 2 for sake of clarity, but it is to be understood that the various features as discussed can be arbitrarily combined. In the embodiment of a hybrid epilator device 100 shown in FIG. 2, the epilation unit 10 is mounted to the housing 101 via a mounting structure 15. The mounting structure 15 has a projection 16 that has a screw thread that meshes with the screw thread of a projection 71 of a stepping motor 70. The control unit 20 controls the stepping motor 70 in such a way that a certain epilation efficiency (lower than the maximal achievable epilation efficiency of the epilation unit 10) is adjusted by retracting the epilation unit 10 from the skin surface 90. The hybrid epilator device 100 has skin contact elements 102 (e.g. realized as a cap structure having an aperture through which the epilation unit 10 can access hairs growing on the skin surface 90) that define a skin contact plane. The epilation unit 10 can now be displaced as indicated by double arrow B from a position in which the epilation unit 10 closely contacts the skin surface 90 to a retracted position (as shown) in which the epilation unit 10 has a certain distance d to the skin surface. Due to this distance d, the epilation efficiency is reduced as e.g. short hairs are not gripped and plucked out from the skin surface 90. Further, razor blades 80 are mounted in a cartridge 81, which cartridge 81 is pivotably mounted to the housing 101 so as to be pivotable around pivot axis 85. The pivotable mounting could also be combined with a floatable mounting as shown in FIG. 1. Due to the pivotable and/or floatable mounting of the razor blade 80, the razor blade 80 stays always in contact with the skin surface to shave off hairs even if the skin surface topology is uneven. It is to be understood that FIGS. 1 and 2 show only exemplary embodiments and instead of three razor blades 80, the hybrid epilator device 100 could be equipped with one, two, four, five etc. razor blades 80 that may be mounted directly at the housing 101 or in a cartridge 81 that is mounted at the housing 101.

Figure 3:
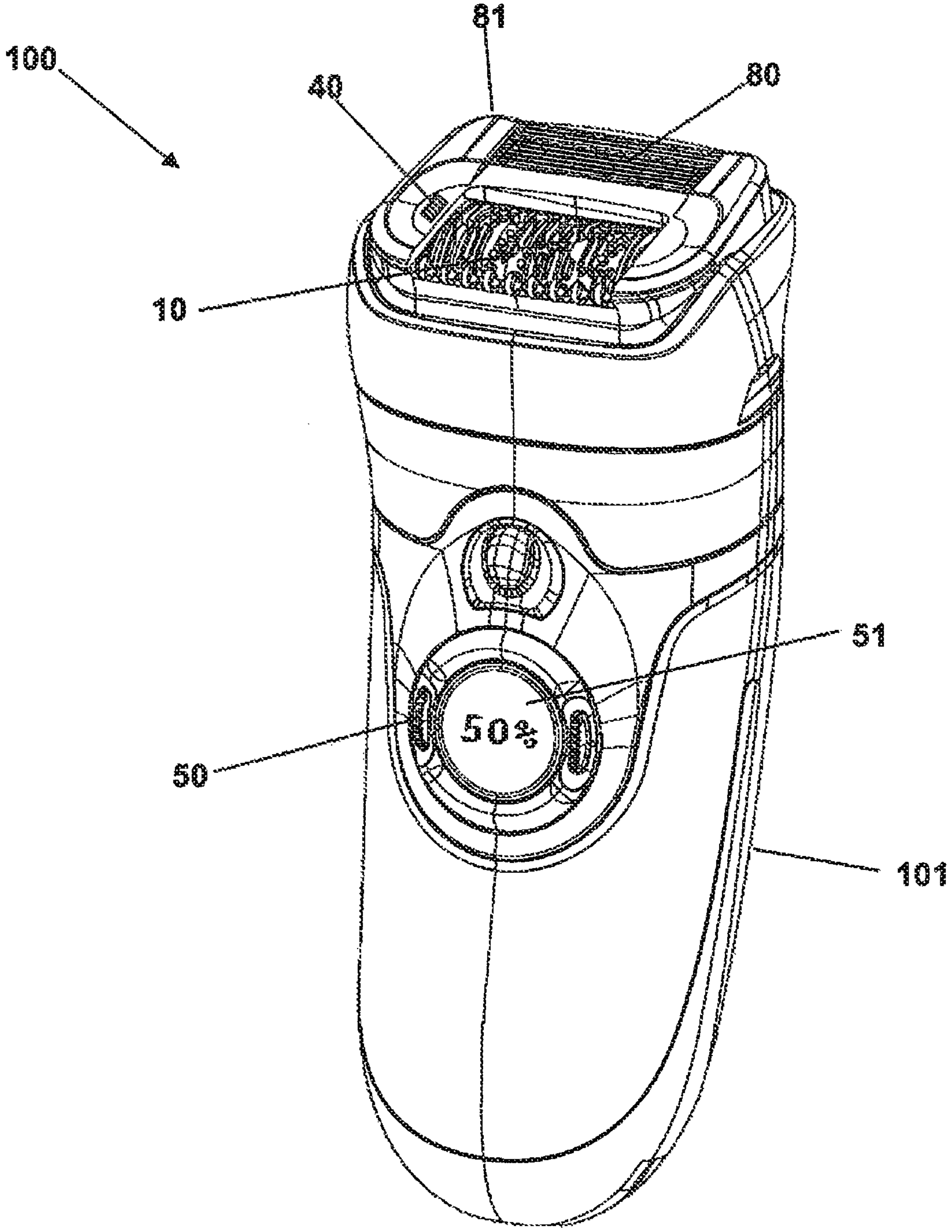
FIG. 3 shows a depiction of an exemplary realization of a hybrid epilator device as proposed.

FIG. 3 is a depiction of a possible realization of a hybrid epilator device 100 as proposed. The hybrid epilator device 100 comprises a housing 101, an epilation unit 10 and a shaving module comprising several razor blades 80. The shaving module is mounted at a cartridge 81 that is realized as a cap element covering the head part of the hybrid epilator device 100. A velocity sensor 40 is integrated into the cartridge near an aperture into which the epilation unit 10 extends. Further, the hybrid epilator device 100 comprises an input unit 50 realized as a control wheel allowing a user to set an epilation efficiency and it comprises a display unit 51 realized as a LCD display on which the set epilation efficiency can be displayed during operation.

In an embodiment of a hybrid epilator device, the epilation unit 10 is arranged to be displaceable, i.e. a stepping motor controlled by the control unit 20 moves the epilation unit 10 such that a distance between the outer surface of the epilation unit 10 and a skin contact surface defined by the cap 81 can be achieved. The farther away the epilation unit 10 is from the skin contact surface (and hence from the skin surface during operation), the lower the epilation efficiency becomes. Instead of having a control unit 20 that controls the displacement, the displacement adjustment could also be done manually, e.g. the epilation unit 10 could be arranged to snap into a proximate position and a distal position.

As stated above, in a hybrid epilator device that comprises an epilation unit and at least a razor blade, the razor blade could be pivotably and/or floatably mounted, either directly or the razor blade could be mounted in a cartridge that is pivotably and/or floatably mounted at the housing of the hybrid epilator device.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:

1. Hybrid epilator device comprising:

a. an epilation unit for gripping and plucking hairs from a skin surface;

b. at least one razor blade having a sharp edge for shaving off hairs growing on the skin surface , the sharp edge of the razor blade defining a use direction (U) along which it is effectuated that hairs are shaved off when the razor blade is drawn over the skin surface in a single stroke during operation of the device, wherein the razor blade is floatingly or pivotally mounted and is in relationship with the epilation unit in a manner that the razor blade trails the epilation unit when the device traverses the skin surface in the in use direction (U) and wherein the epilation unit and the razor blade are affixed to the device in such a manner to simultaneously and continuously contact with the skin surface when the device traverses the skin in the in use direction, and c. a control unit for controlling the epilation unit such that a certain epilation efficiency is achieved;

wherein said control unit is arranged to control the epilation efficiency by controlling the plucking speed of the epilation unit; or wherein the epilation unit comprises at least a pair of tweezers that are arranged to be actuated between an open position in which a gap is present between clamping elements forming the pair of tweezers and a closed position and said control unit controls the epilation efficiency by controlling a parameter of the actuation of said tweezers.

2. Hybrid epilator device according to claim 1 that further comprises an input unit for setting an epilation efficiency value that should be achieved during operation.

3. Hybrid epilator device according to claim 1 that comprises a memory unit in which a preset epilation efficiency value is stored.

4. Hybrid epilator device of claim 1 wherein the epilation unit comprises a cylinder having a rotation speed, wherein the control unit controls the rotation speed thereby controlling the plucking speed.

5. Hybrid epilator device according to claim 1 wherein the parameter of actuation is either the width of the gap between the clamping elements in the open position or an angular position at which the closed position is achieved with respect to a housing of the hybrid epilator device.

6. Hybrid epilator device according to claim 1, wherein the hybrid epilator device comprises a velocity sensor for measuring the velocity of the hybrid epilator device with respect to the skin surface.

7. Hybrid epilator device according, to claim 6, wherein the control unit is arranged to control the epilation efficiency of the epilation unit depending on a velocity signal provided by the velocity sensor.

8. Hybrid epilator device according to claim 1, wherein the razor blade is mounted in a cartridge.

9. Hybrid epilator device comprising a. an epilation unit for gripping and plucking hairs from a skin surface;

b. at least one razar blade having a sharp edge for shaving off hairs growing on the skin surface, the sharp edge of the razor blade defining a use direction (U) along which it is effectuated that hairs are shaved off when the razor blade is drawn over the skin surface in a single stroke during operation of the device, wherein the razor blade is in relationship with the epilation unit in a manner that the razor blade trails the epilation unit when the device traverses the skin surface in the in use direction (U) and wherein the epilation unit and the razor blade are affixed to the device in such a manner to simultaneously and continuously contact with the skin surface when the device traverses the skin in the use direction;

c. a control unit for controlling the epilation unit such that a certain epilation efficiency is achieved;

d. an input unit for setting an epilation efficiency value that should be achieved during operation; and e. a memory unit in which a preset epilation efficiency value is stored;

wherein the control unit is arranged to control the epilation efficiency by controlling the plucking speed of said epilation unit and wherein the epilation unit comprises a cylinder having a rotation speed, wherein the control unit controls the rotation speed; or wherein the epilation unit comprises at least a pair of tweezers that is arranged to be actuated between an open position in which a gap is present between clamping elements forming the pair of tweezers and a closed position and the control unit controls the epilation efficiency by controlling a parameter of the actuation, said parameter being either the width of the gap between the clamping elements in the open position or an angular position at which the closed position is achieved with respect to a housing of the hybrid epilator device.

10. Hybrid epilator device according to claim 9 wherein the hybrid epilator device comprises a velocity sensor for measuring the velocity of the hybrid epilator device with respect to the skin surface.

11. Hybrid epilator device according to claim 10, wherein the control unit is arranged to control the epilation efficiency of the epilation unit in dependence on as velocity signal provided by the velocity sensor.

12. Hybrid epilator device according to claim 9, wherein the razor blade is mounted in a cartridge that is floatingly or pivotably mounted with respect to the housing of the hybrid epilator device.

* * * * *